(12) United States Patent
Toseland et al.

(10) Patent No.: US 7,766,986 B2
(45) Date of Patent: **\*Aug. 3, 2010**

(54) DEHYDROGENATION OF LIQUID FUEL IN MICROCHANNEL CATALYTIC REACTOR

(75) Inventors: Bernard Allen Toseland, Coopersburg, PA (US); Guido Peter Pez, Allentown, PA (US); Pushpinder Singh Puri, Emmaus, PA (US)

(73) Assignee: Air Products & Chemicals, Inc., Allentown, PA (US)

( \* ) Notice: Subject to any disclaimer, the term of this patent is extended or adjusted under 35 U.S.C. 154(b) by 0 days.

This patent is subject to a terminal disclaimer.

(21) Appl. No.: 12/211,585

(22) Filed: Sep. 16, 2008

(65) Prior Publication Data

US 2009/0019768 A1    Jan. 22, 2009

Related U.S. Application Data

(63) Continuation of application No. 11/029,059, filed on Jan. 4, 2005, now Pat. No. 7,485,161.

(51) Int. Cl.
*B01J 7/00* (2006.01)
*B01J 8/04* (2006.01)
*C01B 3/02* (2006.01)

(52) U.S. Cl. ............... 48/61; 422/188; 422/198; 422/190; 423/644; 423/648.1

(58) Field of Classification Search ............ 422/188, 422/198, 190; 48/61, 199 R; 423/644, 648.1
See application file for complete search history.

(56) References Cited

U.S. PATENT DOCUMENTS 4,626,342 A    12/1986    Garg et al.

(Continued)

FOREIGN PATENT DOCUMENTS

EP    1475349 A2    11/2004

(Continued)

OTHER PUBLICATIONS

Chen, G, et al, Hydrogen Generation by Methanol Autothermal Reforming in Microchannel Reactors,: American Institute of Chemical Engineers, Spring Meeting; Mar.-Apr. 2003; pp. 1939-1943.
Scherer, et al; "Economic Analysis of the Seasonal Storage of Electricity with Liquid Organic Hydrides;" International Journal of Hydrogen Energy 24 (1999) pp. 1157-1169.
Clar, E., "Polycyclic Hydrocarbons;" Academic Press; 1964; Chapter 6, vol. 1; pp. 31-39.

(Continued)

*Primary Examiner*—Walter D Griffin
*Assistant Examiner*—Lessanework Seifu
(74) *Attorney, Agent, or Firm*—Michael K. Boyer (57) ABSTRACT

The present invention is an improved process for the storage and delivery of hydrogen by the reversible hydrogenation/dehydrogenation of an organic compound wherein the organic compound is initially in its hydrogenated state. The improvement in the route to generating hydrogen is in the dehydrogenation step and recovery of the dehydrogenated organic compound resides in the following steps:

introducing a hydrogenated organic compound to a microchannel reactor incorporating a dehydrogenation catalyst;

effecting dehydrogenation of said hydrogenated organic compound under conditions whereby said hydrogenated organic compound is present as a liquid phase;

generating a reaction product comprised of a liquid phase dehydrogenated organic compound and gaseous hydrogen;

separating the liquid phase dehydrogenated organic compound from gaseous hydrogen; and, recovering the hydrogen and liquid phase dehydrogenated organic compound.

14 Claims, 1 Drawing Sheet

U.S. PATENT DOCUMENTS

| | | | |
|---|---|---|---|
| 5,300,662 A | 4/1994 | Nishida et al. |
| 6,074,447 A | 6/2000 | Jensen |
| 6,488,838 B1 | 12/2002 | Tonkovich et al. |
| 6,616,909 B1 | 9/2003 | Tonkovich et al. |
| 6,802,875 B1 | 10/2004 | Kimbara et al. |
| 7,351,395 B1 | 4/2008 | Pez et al. |
| 2003/0072699 A1 | 4/2003 | Tonkovich et al. |
| 2003/0180216 A1 | 9/2003 | TeGrotenhuis et al. |
| 2003/0219903 A1 | 11/2003 | Wang et al. |
| 2004/0013606 A1 | 1/2004 | Tonkovich et al. |
| 2004/0033455 A1 | 2/2004 | Tonkovich et al. |
| 2004/0034111 A1 | 2/2004 | Tonkovich et al. |
| 2004/0034266 A1 | 2/2004 | Brophy et al. |
| 2004/0082804 A1 | 4/2004 | Brophy et al. |
| 2004/0199039 A1 | 10/2004 | Brophy et al. |
| 2004/0220434 A1 | 11/2004 | Brophy et al. |
| 2004/0223907 A1 | 11/2004 | Pez et al. |
| 2005/0002857 A1 | 1/2005 | Pez et al. |
| 2005/0013767 A1 | 1/2005 | Bagzis et al. |

FOREIGN PATENT DOCUMENTS

| | | | |
|---|---|---|---|
| JP | 201110437 | | 4/2001 |
| JP | 2002134141 | | 5/2002 |
| JP | 2003-299947 | A | 10/2003 |
| JP | 2003-321201 | A | 11/2003 |
| JP | 2004324784 | | 11/2004 |
| WO | 2005063832 | A2 | 6/2005 |

OTHER PUBLICATIONS

Cooper et al; "Hydrogen Storage and Delivery by Reversible Hydrogenation of Liquid-Phase Hydrogen Carriers;" Prep. Pap.; Am. Chem. Soc., Div. Fuel Chem; vol. 50; 2005.

Rouge et al; "Microchannel Reactors for Fast Periodic Operation: The Catalytic Dehydration of Isopropanol;" Chemical Engineering Science; vol. 56, Issue 4; 2001; p. 1419-1427.

Angeli et al; "Modeling of Gas-Liquid Catalytic Reactions in Microchannels;" Department of Chemical Engineering, University College London, Torrington Place, London; p. 253-259.

Carpentier et al; "Some Liquid Hold-up Experimental Data in Trickle-Bed Reactors for Foaming and Non-foaming Hydrocarbons;" vol. 21, No. 6; 1975; p. 1213-1218.

Losey et al; "Microfabricated Multiphase Packed-Bed Reactors: Characterization of Mass Transfer and Reactions;" Ind. Eng. Chem. Res.; 2001; vol. 40; p. 2555-2562.

Pascal; "Memoires Presenter A La Societe Chimique;" Bull. Soc. Chim.; Jun. 1921; p. 644-656.

Figure 1

DEHYDROGENATION OF LIQUID FUEL IN MICROCHANNEL CATALYTIC REACTOR

CROSS REFERENCE TO RELATED APPLICATIONS

This Application is a continuation of application Ser. No. 11/029,059, filed on Jan. 4, 2005, now allowed. The disclosure of application Ser. No. 11/029,059 is hereby incorporated by reference.

This application is related to commonly assigned application having U.S. Ser. No. 10/833,484 and a filing date of Apr. 27, 2004, the subject matter of which is incorporated by reference.

STATEMENT REGARDING FEDERALLY SPONSORED RESEARCH OR DEVELOPMENT

This invention was made with government support under Contract Number DE-FG36-05GO15015 between Air Products and Chemicals, Inc. and the U.S. Department of Energy. The Government has certain rights to this invention.

BACKGROUND OF THE INVENTION

Hydrogen fueled vehicles, sometimes referred to as the Freedom Car are receiving considerable interest as part of a plan to reduce the reliance on foreign oil and reduce pollution. There are several current designs of hydrogen cars, with one example being a fuel cell powered vehicle commonly called an FCV. In the FCV, hydrogen is supplied to a fuel cell which produces electricity, which is used to power electric motors that propel the vehicle. Another type of hydrogen car is based upon a hydrogen internal combustion engine (HICE). In both designs, hydrogen is the fuel source with water being generated as the combustion byproduct.

A central issue with respect to both types of hydrogen vehicles, i.e., the FCV and HICE vehicles, is one of fuel supply. Not only is there a large infrastructure required for hydrogen dispensation, if one considers all the service stations, production and distribution equipment that are required, but there are issues with respect to fuel handling and use of the fuel on the vehicle itself. Before there can be a progression to dedicated fuel cell propulsion systems and hydrogen internal combustion engines, one must foresee a fuel infrastructure.

Two sources of hydrogen for use in hydrogen cars include the reforming of natural gas (fossil fuels) or from water using electrolysis. Once hydrogen gas is generated it must be stored for subsequent filling of cars or converted into a liquid fuel. Storage of hydrogen gas requires compression and transfer to a cylinder storage vessel. And, if the gaseous hydrogen is stored on the vehicle, such storage cylinders are expensive and they can represent a possible safety hazard in the case of an accident. Alternatively, hydrogen can be stored under low pressure in metal hydride canisters, but, at present, hydride canisters are a lot more expensive than cylinders.

Liquid methanol and other alcohols have been touted as particularly attractive hydrogen sources because they can be catalytically converted over a catalyst allowing pure hydrogen to be released on demand. On site conversion of liquid fuels to gaseous hydrogen overcomes the disadvantages of gaseous storage. Further, fuels such as methanol, and other alcohols are not overly expensive and there is an infrastructure in place today that allows for handling of liquid fuels. Although methanol and alcohols are suitable as a fuel source, they are consumed in the combustion process. In addition, the byproducts of such catalytic conversion, carbon dioxide and water, cannot easily be converted back to a hydrogen source.

Representative patents illustrating hydrogen storage and use are as follows:

*Hydrogen Generation by Methanol Autothermal Reforming In Microchannel Reactors*, Chen, G., et al, American Institute of Chemical Engineers, Spring Meeting, Mar. 30-Apr. 3, 2003 pages 1939-1943 disclose the use of a microchannel reactor as a means for conducting the endothermic steam-reforming reaction and exothermic partial oxidation reaction. Both reactions are carried out in the gas phase.

Scherer, G. W. et al, Int. J. Hydrogen Energy, 1999, 24, 1157 disclose the possibility of storing and transporting hydrogen for energy storage via the catalytic gas phase hydrogenation and the gas phase, high temperature, dehydrogenation of common aromatic molecules, e.g., benzene and toluene.

US 2004/0199039 discloses a method for the gas phase dehydrogenation of hydrocarbons in narrow reaction chambers and integrated reactors. Examples of hydrocarbons for dehydrogenation include propane and isobutane to propylene and isobutene, respectively. Reported in the publication are articles by Jones, et al, and Besser, et al, who describe the gaseous dehydrogenation of cyclohexane in a microreactor. Jones, et al employ a reported feed pressure of 150 kPa and an exit pressure of 1 Pa.

U.S. Pat. No. 6,802,875 discloses a hydrogen supply system for a fuel cell which includes a fuel chamber for storing a fuel such as isopropyl alcohol, methanol, benzene, methylcyclohexane, and cyclohexane, a catalytic dehydrogenation reactor, a gas-liquid separation device wherein byproduct is liquefied and separated from the gaseous dehydrogenation reaction product, and a recovery chamber for the hydrogen and dehydrogenated byproduct.

BRIEF SUMMARY OF THE INVENTION

The present invention provides an improved process for the storage and delivery of hydrogen by the reversible hydrogenation/dehydrogenation of an organic compound wherein the organic compound initially is in its fully or partially hydrogenated state. It is subsequently catalytically dehydrogenated and the reaction product comprised of hydrogen and byproduct dehydrogenated or partially dehydrogenated organic compound is recovered. The improvement in a route to generating hydrogen via dehydrogenation of the organic compound and recovery of the dehydrogenated or partially dehydrogenated organic compound resides in the following steps:

introducing a hydrogenated organic compound, typically a hydrogenated substrate which forms a pi-conjugated substrate on dehydrogenation, to a microchannel reactor incorporating a dehydrogenation catalyst;

effecting dehydrogenation of said hydrogenated organic compound under conditions whereby said hydrogenated organic compound is present in a liquid phase;

generating a reaction product comprised of a liquid phase dehydrogenated organic compound and gaseous hydrogen;

separating the liquid phase dehydrogenated organic compound from gaseous hydrogen; and, recovering the hydrogen and liquid phase dehydrogenated organic compound.

Significant advantages can be achieved by the practice of the invention and these include:

an ability to carry out the dehydrogenation of a liquid organic compound and generate hydrogen at desired delivery pressures;

an ability to carry out dehydrogenation under conditions where the liquid organic fuel source and dehydrogenated liquid organic compound remain in the liquid phase, thus eliminating the need to liquefy or quench the reaction byproduct;

an ability to employ extended pi-conjugated substrates as a liquid organic fuel of reduced volatility in both the hydrogenated and dehydrogenated state, thus easing the separation of the released hydrogen for subsequent usage;

an ability to carry out dehydrogenation under conditions where there is essentially no entrainment of the hydrogenated organic compound such as the hydrogenated pi-conjugated substrate fuel source and dehydrogenated reaction product in the hydrogen product;

an ability to carry out dehydrogenation in small catalytic reactors suited for use in motor vehicles;

an ability to generate hydrogen without the need for excessively high temperatures and pressures and thereby reduce safety concerns; and an ability to use waste heat from the fuel cell or an IC engine for liberating the hydrogen.

DETAILED DESCRIPTION OF THE INVENTION

In the process described herein, the fuel source is an organic compound which can be catalytically dehydrogenated forming carbon-carbon unsaturated bonds under liquid phase conditions at modest temperatures. The fuel source can further be described as one that has a low vapor pressure in order to avoid entrainment and loss of liquid fuel in the hydrogen product. Preferably, the vapor pressure is less than 10 millimeters mercury at 200° C.

In copending application U.S. Ser. No. 10/833,484 having a filing date of Apr. 27, 2004 which has been incorporated by reference, Pi-conjugated (often written in the literature using the Greek letter Π) several molecules are suggested as fuel sources of hydrogen which are in the form of liquid organic compounds. These Pi-conjugated substrates are characteristically drawn with a sequence of alternating single and double bonds. In molecular orbital theory, the classically written single bond between two atoms is referred to as a σ-bond, and arises from a bonding end-on overlap of two dumbbell shaped "p" electron orbitals. It is symmetrical along the molecular axis and contains the two bonding electrons. In a "double" bond, there is, in addition, a side-on overlap of two "p" orbitals that are perpendicular to the molecular axis and is described as a pi-bond (or "Π-bond"). It also is populated by two electrons but these electrons are usually less strongly held, and more mobile. The consequence of this is that these pi-conjugated molecules have a lower overall energy, i.e., they are more stable than if their pi-electrons were confined to or localized on the double bonds.

The practical consequence of this additional stability is that hydrogen storage and delivery via catalytic hydrogenation/dehydrogenation processes are less energy intensive and can be carried out at mild temperatures and pressures. This is represented by the following. The most common highly conjugated substrates are the aromatic compounds, benzene and naphthalene. While these can be readily hydrogenated at, e.g., 10-50 atm. at $H_2$ at ca 150° C. in the presence of appropriate catalysts, extensive catalytic dehydrogenation of cyclohexane and decahydronaphthalene (decalin) at atmospheric pressure is only possible at excessively high temperatures leading to gas phase conditions.

For the purposes of this description regarding suitable organic compounds suitable as hydrogen fuel sources, "extended pi-conjugated substrates" are defined to include extended polycyclic aromatic hydrocarbons, extended pi-conjugated substrates with nitrogen heteroatoms, extended pi-conjugated substrates with heteroatoms other than nitrogen, pi-conjugated organic polymers or oligomers, ionic pi-conjugated substrates, pi-conjugated monocyclic substrates with multiple nitrogen heteroatoms, pi-conjugated substrates with at least one triple bonded group and selected fractions of coal tar or pitch that have as major components the above classes of pi-conjugated substrates, or any combination of two or more of the foregoing.

In one embodiment, the pi-conjugated substrates have a standard enthalpy change of hydrogenation, $|\Delta H°_{H2}|$, to their corresponding saturated counterparts (e.g., the at least partially hydrogenated extended pi-conjugated substrates) of less than about 20 kcal/mol $H_2$ and generally less than 15.0 kcal/mol $H_2$. This value can be determined by combustion methods or by the ab initio DFT method. For purposes of the hydrogenation/dehydrogenation cycle to store and release hydrogen and to re-hydrogenate the substrate, the extended pi-conjugated substrate may exist and be cycled between different levels of full or partial hydrogenation and dehydrogenation as to either the individual molecules or as to the bulk of the substrate, depending upon the degree of conversion of the hydrogenation and dehydrogenation reactions.

The liquid phase pi-conjugated substrates useful according to this invention may also have various ring substituents, such as -n-alkyl, -branched-chain alkyl, -alkoxy, -nitrile, -ether and -polyether, which may improve some properties such as reducing the melting temperature of the substrate while at the same time not adversely interfering with the hydrogenation/dehydrogenation equilibrium. Preferably, any of such substituent groups would have 12 or less carbons. As discussed below in the section on "Pi-conjugated Substrates with Multiple Nitrogen Heteroatoms" alkyl substituents (and it's expected that also alkoxy substituents) will actually favorably slightly lower the modulus of the heat of hydrogenation, $\Delta H°_{H2}$.

Extended Pi-Conjugated Substrates

Classes of extended pi-conjugated substrates suitable for the processes of this invention are further and more specifically defined as follows:

Extended Polycyclic Aromatic Hydrocarbons (EPAH). For the purposes herein, "extended polycyclic aromatic hydrocarbons" are defined to be those molecules having either (1) a polycyclic aromatic hydrocarbon comprising a fused ring system having at least four rings wherein all rings of the fused ring system are represented as 6-membered aromatic sextet structures; or (2) a polycyclic aromatic hydrocarbon of more than two rings comprising a six-membered aromatic sextet ring fused with a 5-membered ring.

The EPAH molecules represent a particular class of extended pi-conjugated substrates since their pi electrons are largely delocalized over the molecule. While, on a thermodynamic basis, generally preferred are the larger molecules (i.e., those with considerably more than four rings), the value of the standard enthalpy change of hydrogenation, $\Delta H°_{H2}$, and thus the ease of reversible hydrogenation can be very dependent on the "external" shape or structure of the EPAH molecule.

Fundamentally, the EPAH molecules that have the highest aromatic resonance stabilization energy will have the lowest modulus (absolute value) of the standard enthalpy of hydrogenation, $\Delta H°_{H2}$. As is taught by E. Clar in "Polycyclic Hydrocarbons" Academic Press, 1964, Chapter 6, it is a general principle that the stability of isomers of fused ring substrates increases with the number of aromatic sextets. For instance anthracene has one aromatic sextet (conventionally represented by three alternating single and double bonds in a single ring or by an internal circle), as for benzene, while phenanthrene, has two aromatic sextets, with the result that phenanthrene is more stable by 4.4 kcal/mol (based on the molecules' relative heats of formation).

For an EPAH of a given number of fused rings the structural isomer that is represented with the largest number of aromatic sextets and yet remain liquid at reaction temperatures will be preferred as a hydrogenation/dehydrogenation extended pi-conjugated substrate. Non-limiting examples of polycyclic aromatic hydrocarbons or derivatives thereof particularly useful as a fuel source include pyrene, perylene, coronene, ovalene, picene and rubicene.

EPAH's comprising 5-membered rings are defined to be those molecules comprising a six-membered aromatic sextet ring fused with a 5-membered ring. Surprisingly, these pi-conjugated substrates comprising 5-membered rings provide effective reversible hydrogen storage substrates since they have a lower modulus of the $\Delta H°$ of hydrogenation than the corresponding conjugated system in a 6-membered ring. The calculated (PM3) $\Delta H°$ for hydrogenation of three linear, fused 6-membered rings (anthracene) is −17.1 kcal/mol $H_2$. Replacing the center 6-membered ring with a 5-membered ring gives a molecule (fluorene, $C_{13}H_{10}$)

Non-limiting examples of fused ring structures having a five-membered ring include fluorene, indene and acenanaphthylene.

Extended polycyclic aromatic hydrocarbons can also include structures wherein at least one of such carbon ring structures comprises a ketone group in a ring structure and the ring structure with the ketone group is fused to at least one carbon ring structure which is represented as an aromatic sextet. Introducing a hydrogenable ketone substituent into a polyaromatic substrate with which it is conjugated, acceptable heats and hydrogen storage capacities are achievable. Thus for the pigment pyranthrone, having a standard calculated enthalpy of hydrogenation is −14.4 kcal/mol $H_2$.

Extended Pi-conjugated Substrates with Nitrogen Heteroatoms can also be used as a fuel source. Extended pi-conjugated substrates with nitrogen heteroatoms are defined as those N-heterocyclic molecules having (1) a five-membered cyclic unsaturated hydrocarbon containing a nitrogen atom in the five membered aromatic ring; or (2) a six-membered cyclic aromatic hydrocarbon containing a nitrogen atom in the six membered aromatic ring; wherein the N-heterocyclic molecule is fused to at least one six-membered aromatic sextet structure which may also contain a nitrogen heteroatom.

It has been observed that the overall external "shape" of the molecule can greatly affect the standard enthalpy of hydrogenation, $\Delta H°$. The N heteroatom polycyclic hydrocarbons that contain the greatest number of pyridine-like aromatic sextets will be the most preferred structure and have the lowest modulus of the standard enthalpy of hydrogenation $\Delta H°_{H2}$ structures. The incorporation of two N atoms in a six membered ring (i.e., replacing carbons) provides an even further advantage, the effect on $\Delta H°_{H2}$ depending on the nitrogens' relative positional substitution pattern. A particularly germane example is provided by 1,4,5,8,9,12-hexaazatriphenylene, $C_{18}H_6N_6$, and its perhydrogenated derivative, $C_{12}H_{24}N_6$ system for which the (DFT calculated) $\Delta H°_{H2}$ of hydrogenation is −11.5 kcal/mol $H_2$ as compared to the (DFT calculated) $\Delta H°_{H2}$ of hydrogenation of −14.2 kcal/mol $H_2$ for the corresponding all carbon triphenylene, perhydrotriphenylene system. Another representative example is pyrazine[2,3-b]pyrazine:

where the (DFT calculated) of $\Delta H°_{H2}$ of hydrogenation is −12.5 kcal/mol $H_2$.

Pi-conjugated aromatic molecules comprising five membered rings substrate classes identified above and particularly where a nitrogen heteroatom is contained in the five membered ring provide the lowest potential modulus of the $\Delta H°_{H2}$ of hydrogenation of this class of compounds and are therefore effective substrates for dehydrogenation in a microchannel reactor under liquid phase conditions according to this invention. Non-limiting examples of polycyclic aromatic hydrocarbons with a nitrogen heteroatom in the five-membered ring fitting this class include the N-alkylindoles such as N-methylindole, 1-ethyl-2-methylindole; N-alkylcarbazoles such as N-methylcarbazole and N-propylcarbazole; indolocarbazoles such as indolo[2,3-b]carbazole; and indolo[3,2-a] carbazole; and other heterocyclic structure with a nitrogen atom in the 5- and 6-membered rings such as N,N',N"-trimethyl-6,11-dihydro-5H-diindolo[2,3-a:2',3'-c]carbazole, 1,7-dihydrobenzo[1,2-b:5,4-b']dipyrrole, and 4H-benzo[def]carbazole.

Extended pi-conjugated substrates with nitrogen heteroatoms can also comprise structures having a ketone group in the ring structure, wherein the ring structure with the ketone group is fused to at least one carbon ring structure which is represented as an aromatic sextet. An example of such structure is the molecule flavanthrone, a commercial vat dye, a polycyclic aromatic that contains both nitrogen heteroatoms and keto groups in the ring structure, and has a favorable (PM3 calculated) $\Delta H°$ of hydrogenation of −13.8 kcal/mol $H_2$ for the addition of one hydrogen atom to every site including the oxygen atoms.

Extended Pi-conjugated Substrates with Heteroatoms other than Nitrogen can also be used as a fuel source and for purposes of this description "extended pi-conjugated substrates with heteroatoms other than nitrogen" are defined as those molecules having a polycyclic aromatic hydrocarbon comprising a fused ring system having at least two rings wherein at least two of such rings of the fused ring system are represented as six-membered aromatic sextet structures or a five-membered pentet wherein at least one ring contains a heteroatom other than nitrogen. An example of an extended pi-conjugated substrate with an oxygen heteroatom is dibenzofuran, $C_{12}H_8O$, for which the (DFT calculated) $\Delta H°_{H2}$ of hydrogenation is −13.5 kcal/mol $H_2$. An example of a extended pi-conjugated substrate with a phosphorous heteroatom is phosphindol-1-ol:

An example of a extended pi-conjugated substrate with a silicon heteroatom is silaindene:

An example of a extended pi-conjugated substrate with a boron heteroatom is borafluorene:

Non-limiting examples of extended pi-conjugated substrates with heteroatoms other than nitrogen include dibenzothiophene, 1-methylphosphindole, 1-methoxyphosphindole, dimethylsilaindene, and methylboraindole.

Pi-conjugated Organic Polymers and Oligomers Containing Heteroatoms can also be used as a fuel source. For the purposes of this description the, "pi-conjugated organic polymers and oligomers containing heteroatoms" are defined as those molecules comprising at least two repeat units and containing at least one ring structure represented as an aromatic sextet of conjugated bonds or a five membered ring structure with two double bonds and a heteroatom selected from the group consisting of boron, nitrogen, oxygen, silicon, phosphorus and sulfur. Oligomers will usually be molecules with 3-12 repeat units. While there are often wide variations in the chemical structure of monomers and, often, the inclusion of heteroatoms (e.g., N, S, O) replacing carbon atoms in the ring structure in the monomer units, all of these pi-con- jugated polymers and oligomers have the common structural features of chemical unsaturation and an extended conjugation. Generally, while the molecules with sulfur heteroatoms may possess the relative ease of dehydrogenation, they may be disfavored in fuel cell applications because of the potential affects of the presence of trace sulfur atoms.

The chemical unsaturation and conjugation inherent in this class of polymers and oligomers represents an extended pi-conjugated system, and thus these pi-conjugated polymers and oligomers, particularly those with nitrogen or oxygen heteroatoms replacing carbon atoms in the ring structure, are a potentially suitable substrate for hydrogenation. These pi-conjugated organic polymers and oligomers may comprise repeat units containing at least one aromatic sextet of conjugated bonds or may comprise repeat units containing five membered ring structures. Aromatic rings and small polyaromatic hydrocarbon (e.g., naphthalene) moieties are common in these conducting polymers and oligomers, often in conjugation with heteroatoms and/or olefins. For example, a heteroaromatic ladder polymer or oligomer containing repeat units such as:

which contains a monomer with a naphthalene moiety in conjugation with unsaturated linkages containing nitrogen atoms.

A pi-conjugated polymer or oligomer formed from a derivatised carbazole monomer repeat unit, can also be used as a fuel source. Other oligomers that contain 5-membered ring structures with nitrogen atoms are also subject of the present invention. For example, oligomers of pyrrole such as:

which has four pyrrole monomers terminated by methyl groups has an ab initio DFT calculated $\Delta H°_{H2}$ of hydrogenation of $-12.5$ kcal/mol $H_2$. Other members of this class of pi-conjugated organic polymers and oligomers which are particularly useful according to this invention as extended pi-conjugated substrates are polyindole, polyaniline, poly(m-ethylcarbazole), and poly(9-vinylcarbazole).

Ionic Pi-conjugated Substrates can also be used as fuel source, i.e., a hydrogen source. These ionic pi-conjugated substrates are defined as those substrates having pi-conjugated cations and/or anions that contain unsaturated ring systems and/or unsaturated linkages between groups. Pi-conjugated systems which contain a secondary amine function, $HNR_2$ can be readily deprotonated by reaction with a strong base, such as lithium or potassium hydride, to yield the corresponding lithium amide or potassium amide salt. Examples of such systems include carbazole, imidazole and pyrrole and N-lithium carbazole. Non-limiting examples of ionic pi-conjugated substrates include N-lithiocarbazole, N-lithioindole, and N-lithiodiphenylamine and the corresponding N-sodium, N-potassium and N-tetramethylammonium compounds.

Pi-conjugated monocyclic substrates with multiple nitrogen heteroatoms are another form of hydrogen fuel source. For the purposes of this description "pi-conjugated monocyclic substrates with multiple nitrogen heteroatoms" are defined as those molecules having a five-membered or six-membered aromatic ring having two or more nitrogen atoms in the aromatic ring structure, wherein the aromatic ring is not fused to another aromatic ring. The pi-conjugated monocyclic substrates with multiple nitrogen heteroatoms may have alkyl, N-monoalkylamino and N,N-dialkylamino substituents on the ring. A non-limiting example of a pi-conjugated monocyclic substrates with multiple nitrogen heteroatoms is pyrazine.

Pi-conjugated substrates with triply bonded groups can be used as a fuel source. For the purposes of this description, "pi-conjugated substrates with triply bonded groups" are defined as those molecules having carbon-carbon and carbon-nitrogen triple bonds. The pi-conjugated molecules described thus far comprise atom sequences conventionally written as alternating carbon-carbon single, and carbon-carbon double bonds, i.e., C—C=C—C=C— etc., incorporating, at times, carbon-nitrogen double bonds, i.e., imino groups as in the sequence, C—C=N—C=C—.

An illustration is provided by 1,4-dicyanobenzene:

which can be reversibly hydrogenated to 1,4-aminomethyl cyclohexane:

The enthalpy for this reaction, $\Delta H°_{H2}$, is $-16.4$ kcal/mol $H_2$.

Table 1a. provides representative extended polycyclic aromatic hydrocarbon substrates, some of which can be used as a liquid hydrogen fuel source or converted to a liquid by incorporating substituents groups such as alkyl groups on the substrate and relevant property data therefor. Comparative data for benzene (1), naphthalene (2, 3), anthracene (46) and phenanthrene (47).

TABLE 1a

| Substrate Number | Substrate Structure | ΔH$_{H2}$° (300 K) (cal.) | ΔH$_{H2}$° (298 K) (exp.) | T$_{95\%}$ °C. (cal.) | T$_{95\%}$ °C. (exp.) |
|---|---|---|---|---|---|
| 1 |  | −15.6 | −16.42 | 319 | 318 |
| 2[a] |  cis | −15.1 | −15.29 | 244 | 262 |
| 3[b] |  trans | −15.8 | −15.91 | 273 | 280 |
| 6 |  | −14.6 | | 226 | |
| 7 |  | −13.0 | | 169 | |
| 22 |  | −13.9 | | 206 | |
| 26 |  | −52.2 | | | |
| 27 |  | −17.9 | | 333 | |
| 28 |  | −14.4 | | 223 | |
| 31 |  | −14.1 | | 216 | |

TABLE 1a-continued

| Substrate Number | Substrate Structure | ΔH$_{H2}$° (300 K) (cal.) | ΔH$_{H2}$° (298 K) (exp.) | T$_{95\%}$ °C. (cal.) | T$_{95\%}$ °C. (exp.) |
|---|---|---|---|---|---|
| 34 |  | −14.2 | | 216 | |
| 46 |  | −15.8 | | 271 | |
| 47 |  | −14.8 | | 237 | |

$^a$Heat of hydrogenation to form cis-decalin.
$^b$Heat of hydrogenation to form the trans-decalin.

Table 1b shows extended pi-conjugated substrates with nitrogen heteroatoms some of which may be liquids or converted to liquids and thus suited as a hydrogen fuel source. Property data are included.

TABLE 1b

| Substrate Number | Substrate Structure | ΔH$_{H2}$° (300 K) (cal.) | ΔH$_{H2}$° (298 K) (exp.) | T$_{95\%}$ °C. (cal.) | T$_{95\%}$ °C. (exp.) |
|---|---|---|---|---|---|
| 4 |  | −13.2 | −13.37 | 248 | 274 |
| 5 |  | −15.2 | −14.96 | 268 | 262 |
| 8 |  | −12.2 | | 153 | |
| 9 |  | −11.9 | | 164 | |
| 10 |  | −12.5 | | 182 | |

TABLE 1b-continued

| Substrate Number | Substrate Structure | $\Delta H_{H2}°$ (300 K) (cal.) | $\Delta H_{H2}°$ (298 K) (exp.) | $T_{95\%}$ °C. (cal.) | $T_{95\%}$ °C. (exp.) |
| --- | --- | --- | --- | --- | --- |
| 11 | | −11.2 | | 117 | |
| 12 | | −10.6 | | 96 | |
| 13 | | −10.7 | | 87 | |
| 14 | | −11.4 | | 131 | |
| 15 | | −14.4 | | 225 | |
| 16 | | −11.5 | | 124 | |
| 17 | | −9.7 | | 66 | |
| 18 | | −11.7 | | 132 | |

TABLE 1b-continued

| Substrate Number | Substrate Structure | $\Delta H_{H2}°$ (300 K) (cal.) | $\Delta H_{H2}°$ (298 K) (exp.) | $T_{95\%}$ °C. (cal.) | $T_{95\%}$ °C. (exp.) |
| --- | --- | --- | --- | --- | --- |
| 19 | (structure) | −8.7 | | 27 | |
| 20 | (structure) | −12.1* | −12.4* | 128 | 128 |
| 21 | (structure) | −12.4 | | 164 | |
| 23 | (structure) | −14.2 | | 220 | |
| 24 | (structure) | −14.8 | | 239 | |
| 25 | (structure) | −12.5 | | 168 | |
| 30 | (structure) | −12.2 | | 139 | |
| 35 | (structure) | −13.8 | | 201 | |

TABLE 1b-continued

| Substrate Number | Substrate Structure | ΔH$_{H2}°$ (300 K) (cal.) | ΔH$_{H2}°$ (298 K) (exp.) | T$_{95\%}$ °C. (cal.) | T$_{95\%}$ °C. (exp.) |
| --- | --- | --- | --- | --- | --- |
| 36 |  | −15.1 | | 245 | |
| 37 |  | −12.5 | | 163 | |
| 38 |  | −15.2 | | 413 | |
| 39 |  | −9.9 | | 82 | |
| 40 |  | −8.8 | | 70 | |
| 41 |  | −6.4 | | | |
| 42 |  | −9.0 | | | |
| 43 |  | −10.5 | | 88. | |

TABLE 1b-continued

| Substrate Number | Substrate Structure | $\Delta H_{H2}°$ (300 K) (cal.) | $\Delta H_{H2}°$ (298 K) (exp.) | $T_{95\%}$ °C. (cal.) | $T_{95\%}$ °C. (exp.) |
|---|---|---|---|---|---|
| 53 | (pyrazine) | −13.5 | | | |
| 54 | (pyrrole fused with two pyrazines, N-H) | −7.7 | | | |

*Calculated and experimental data, both at 150° C.

Table 1c shows extended pi-conjugated substrates with heteroatoms other than nitrogen some of which may be liquids or converted to liquids and thus suited for use as fuels. Property data are included. Comparative data for diphenylsilanes also are shown.

TABLE 1c

| Substrate Number | Substrate Structure | $\Delta H_{H2}°$ (300 K) (cal.) | $\Delta H_{H2}°$ (298 K) (exp.) | $T_{95\%}$ °C. (cal.) | $T_{95\%}$ °C. (exp.) |
|---|---|---|---|---|---|
| 29 | dibenzoborole (B-H) | −10.2 | | 52 | |
| 32 | dibenzofuran | −13.5 | | 197 | |
| 33 | dibenzodioxin | −16.4 | | 285 | |
| 44 | dimethyldiphenylsilane | −15.6 | | 275 | |
| 45 | dimethoxydiphenylsilane | | | 273 | |

TABLE 1c-continued

| Substrate Number | Substrate Structure | $\Delta H_{H2}°$ (300 K) (cal.) | $\Delta H_{H2}°$ (298 K) (exp.) | $T_{95\%}$ °C. (cal.) | $T_{95\%}$ °C. (exp.) |
|---|---|---|---|---|---|
| 55 | benzo-fused phosphole with P–O–H | −17.0 | | | |
| 56 | benzo-fused silole with Si–H₂ | −16.4 | | | |

Table 1d shows pi-conjugated organic polymers and oligomers some of which may be liquids or converted to liquids and thus suited for use as fuels. Property data are included. Comparative data for phenylene oligomers also are shown.

TABLE 1d

| Substrate Number | Substrate Structure | $\Delta H_{H2}°$ (300 K) (cal.) | $\Delta H_{H2}°$ (298 K) (exp.) | $T_{95\%}$ °C. (cal.) | $T_{95\%}$ °C. (exp.) |
|---|---|---|---|---|---|
| 52 | pyrrole pentamer with methyl end groups | −12.5 | | | |
| 57 | N,N-dimethyl-terminated tri(p-phenyleneamine) | −15.1 | | | |
| 48 | biphenyl | −16.0 | | 298 | |
| 49 | p-terphenyl | −15.7 | | | |
| 50 | p-quaterphenyl | −15.6 | | | |
| 51 | m-terphenyl (branched) | −15.8 | | | |

Sometimes one can convert hydrogenated extended pi-conjugated substrates which normally would be solid under reaction conditions to a liquid by utilizing a mixture of two or more components. In some cases, mixtures may form a eutectic mixture. For instance chrysene (1,2-benzophenanthrene, m.p. 250° C.) and phenanthrene, (m.p. 99° C.) are reported to form a eutectic melting at 95.5° C. and for the 3-component system consisting of chrysene, anthracene and carbazole (m.p. 243° C.), a eutectic is observed at 192° C. (Pascal, Bull. Soc. Chim. Fr. 1921, 648). The introduction of n-alkyl, alkyl, alkoxy, ether or polyether groups as substituents on the ring structures of the polycyclic aromatic molecules, particularly the use such substituents of varying chain lengths up to about 12 carbon atoms, often can lower their melting points. But, this may be at some cost in "dead weight" and reduced hydrogen capacity. As discussed above, certain substituents, e.g., nitriles and alkynes, can provide additional hydrogen capacity since each nitrile group can accommodate two molar equivalents of hydrogen.

The dehydrogenation catalysts suited for use in microchannel reactors generally are comprised of finely divided or nanoparticles of metals, and their oxides and hydrides, of Groups 4, 5, 6 and 8, 9, 10 of the Periodic Table according to the International Union of Pure and Applied Chemistry. Preferred are titanium, zirconium of Group 4; tantalum and niobium of Group 5; molybdenum and tungsten of Group 6; iron, ruthenium of Group 8; cobalt, rhodium and iridium of Group 9; and nickel, palladium and platinum of Group 10 of the Periodic Table according to the International Union of Pure and Applied Chemistry. Of these the most preferred being zirconium, tantalum, rhodium, palladium and platinum, or their oxide precursors such as $PtO_2$ and their mixtures, as appropriate.

These metals may be used as catalysts and catalyst precursors as metals, oxides and hydrides in their finely divided form, as very fine powders, nanoparticles or as skeletal structures such as platinum black or Raney nickel, or well-dispersed on carbon, alumina, silica, zirconia or other medium or high surface area supports, preferably on carbon or alumina.

Figure 1:
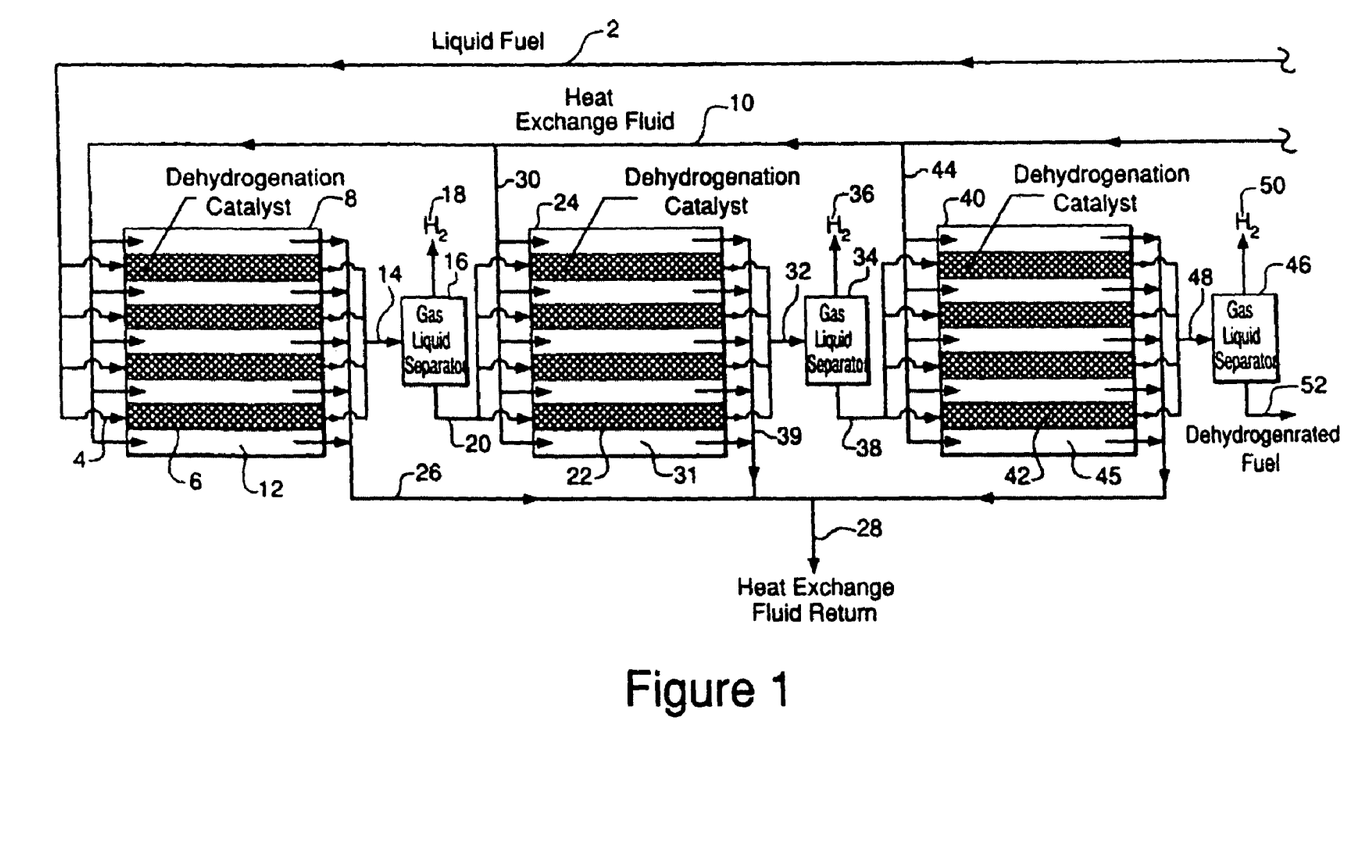
FIG. 1 is a flow diagram of a dehydrogenation process for producing hydrogen from a liquid fuel while maintaining the liquid fuel and dehydrogenated byproduct in liquid phase.

Having described candidates for use a source of hydrogen and their use as fuels for vehicles, their conversion for on site use is described. To facilitate an understanding of the improved step of dehydrogenation of the liquid hydrogen fuel sources described herein, reference is made to FIG. 1. FIG. 1 illustrates the use of three microchannel reactors with serial flow of a liquid fuel through the reactors. This reactor scheme illustrated in the flow diagram has been designed for to provide a constant volume of hydrogen to be generated within each channel of the microchannel reactors.

Microchannel reactors, which term is intended by definition to include monolith reactors, are well suited for the liquid phase dehydrogenation process. They offer ability to effect the dehydrogenation of hydrogen fuel sources while obtaining excellent heat transfer and mass transfer. In gas phase dehydrogenation, their main deficiency has been one of excessive pressure drop across the microchannel reactor. Compression of the gaseous reactants comes at a high cost. However, because, in accordance with this invention, the feed to the microchannel reactors is a liquid, the ability to pressurize the reactor becomes easy. One can pump the liquid fuel to a desired reaction pressure. Thus, pressure drop does not become an insurmountable problem as it is in gas phase production of hydrogen. And, as a benefit of the ability to pressurize, it is easy to generate high-pressure hydrogen as a product of the reaction.

Microchannel reactors and monolith reactors are known in the art. The microchannel reactors are characterized as having at least one reaction channel having a dimension (wall-to-wall, not counting catalyst) of 2.0 mm (preferably 1.0 mm) or less, and in some embodiments 50 to 500 μm. The height and/or width of a reaction microchannel is preferably 2 mm or less, and more preferably 1 mm or less. The channel cross section may be square, rectangular, circular, elliptical, etc. The length of a reaction channel is parallel to flow through the channel. These walls are preferably made of a nonreactive material which is durable and has good thermal conductivity. Most microchannel reactors incorporate adjacent heat transfer microchannels, and in the practice of this invention, such reactor scheme generally is necessary to provide the heat required for the endothermic dehydrogenation. Illustrative microchannel reactors are shown in US 2004/0199039 and U.S. Pat. No. 6,488,838 and are incorporated by reference.

Monolith supports which may be catalytically modified and used for catalytic dehydrogenation are honeycomb structures of long narrow capillary channels, circular, square or rectangular, whereby the generated gas and liquid can co-currently pass through the channels. Typical dimensions for a honeycomb monolith catalytic reactor cell wall spacing range from 1 to 10 mm between the plates. Alternatively, the monolith support may have from 100 to 800, preferably 200 to 600 cells per squared inch (cpi). Channels or cells may be square, hexagonal, circular, elliptical, etc. in shape.

In a representative dehydrogenation process, a liquid fuel 2, such as N-ethyl carbazole, is pressurized by means of a pump (not shown) to an initial, preselected reaction pressure, e.g., 1000 psia and delivered via manifold 4 to a plurality of reaction chambers 6 within a first microchannel reactor 8. (Overall dehydrogenation pressures may range from 0.2 to 100 atmospheres.) As shown, dehydrogenation catalyst particles are packed within the reactor chambers 6, although, as an alternative, the catalyst may be embedded, impregnated or coated onto the wall surface of reaction chambers 6. The reaction channel 6 may be a straight channel or with internal features such that it offers a large surface area to volume of the channel.

Heat is supplied to the microchannel reactor by circulating a heat exchange fluid via line 10 through a series of heat exchange channels 12 adjacent to reaction chambers 6. The heat exchange fluid may be in the form of a gaseous byproduct of combustion which may be generated in a hybrid vehicle or hydrogen internal combustion engine or it may be a heat exchange fluid employed for removing heat from fuel cell operation. In some cases, where a liquid heat exchange fluid is employed, as for example heat exchange fluid from a fuel cell, supplemental heat may be added, by means not shown, through the use of a combustion gas or thermoelectric unit. The heat exchange fluid from a PEM (proton exchange membrane) fuel cell typically is recovered at a temperature of about 80° C., which may be at the low end of the temperature for dehydrogenation. By the use of combustion gases it is possible to raise the temperature of the heat exchange fluid to provide the necessary heat input to support dehydrogenation of many of the fuel sources. A heat exchange fluid from fuel cells that operate at higher temperatures, e.g., 200° C. from a phosphoric acid fuel cell, may also be employed.

In the embodiment shown, dehydrogenation is carried out in microchannel reactor 8 at a temperature of generally from about 60 to 300° C., at some pressure of hydrogen. Dehydrogenation is favored by higher temperatures, elevated temperatures; e.g., 200° C. and above may be required to obtain a desired dehydrogenation reaction rate. Because initial, and partial, dehydrogenation of the liquid fuel source occurs quickly, high pressures are desired in the initial phase of the reaction in order to facilitate control of the liquid to gas ratio that may occur near the exit of the reactor chambers. High gas to liquid ratios in reaction chambers 6 midway to the exit of the reactor chambers can cause the catalyst to dry and, therefore reduce reaction rate. In a favored operation, the residence time is controlled such that Taylor flow is implemented, in those cases where the catalyst is coated onto the wall surface of the reactor, or trickling or pulsating flow is maintained in those cases where the catalyst is packed within the reaction chamber. (The pulsing flow regime is described by many references (e.g. Carpentier, J. C. and Favier, M. AIChE J 1975 21 (6) 1213-1218) for convention reactors and for microchannel reactors by Losey, M. W. et al, Ind. Eng. Chem. Res., 2001, 40, p 2555-2562 and is incorporated by reference.) By appropriate control of the gas/liquid ratio, a thin film of liquid organic compound remains in contact with the catalyst surface and facilitates reaction rate and mass transfer of hydrogen from the liquid phase to the gas phase.

After a preselected initial conversion of liquid fuel in microchannel reactor 8 is achieved, e.g. one-third the volume of the hydrogen to be generated, the reaction product comprised of hydrogen and partially dehydrogenated liquid fuel is sent by line 14 to gas/liquid or phase separator 16. Hydrogen is removed at high pressure as an overhead via line 18 and a high pressure partially dehydrogenated liquid fuel source is removed as a bottoms fraction via line 20. High pressure separation is favored to minimize carry over of unconverted liquid hydrocarbon fuel, which typically has a slightly higher vapor pressure than the dehydrogenated byproduct, and contamination of the hydrogen overhead. Advantageously, then the reaction product need not be quenched and thus rendered liquid in order to effect efficient separation of the partially dehydrogenated organic compound from the hydrogen and minimize carryover into the hydrogenated product. This is a favored feature in contrast to those dehydrogenation processes which use reactants such as isopropanol, cyclohexane and decalin where the dehydrogenation reaction products are in the gas phase.

The bottoms from gas/liquid separator 16 in line 20 is combined and charged to reaction chambers 22 in second microchannel reactor 24 at the same or higher temperature in order to maintain reaction rate. The cooled heat exchange fluid is removed from heat exchange channels 6 via line 26 and returned to the fuel cell, if liquid or, if the hydrogen exchange fluid is combustion gas, then it is often vented to the atmosphere via line 28.

On recovery of the bottoms from gas/liquid separator 16, the resulting and partially dehydrogenated liquid fuel may be further reduced in pressure than normally occurs because of the ordinary pressure drop which occurs in microchannel reactor. The pressure in second microchannel reactor 24 is preselected based upon design conditions but in general a pressure of from 30 to 200 psia can be employed for N-ethyl carbazole. The temperature of the previously but partially dehydrogenated liquid fuel in reaction chambers 22 is maintained in second microchannel reactor. Heat to second microchannel reactor 24 is supplied from heat exchange fluid line 10 via manifold 30 to heat exchange channels 31. The use of a lower operating pressure in second microchannel reactor 24 than employed in the first microchannel reactor 8 allows for significant dehydrogenation at the design reaction temperature. Again conversion is controlled in second microchannel reactor in order to provide for a desirable liquid to gas ratio particularly as the reaction product approaches the end of the reaction chamber. The reaction product comprised of hydrogen and further partially dehydrogenation is removed via manifold 32 and separated in gas/liquid separator 34. Hydrogen is removed as an overhead from gas/liquid separator 34 via line 36 and a further dehydrogenated liquid fuel is removed from the bottom of gas/liquid separator 34 via line 38. Heat exchange fluid is withdrawn via line 39 from microchannel reactor 24 and returned to heat exchange fluid return in line 28.

The final stage of dehydrogenation is carried out in third microchannel reactor 40. The partially dehydrogenated liquid fuel in line 38 is introduced as liquid to reaction chambers 42 at the same or higher temperature, based on design. Heat is supplied for the endothermic reaction by heat exchange fluid in line 10 via manifold 44 to heat exchange channels 45. As the dehydrogenation approaches equilibrium in final microchannel reactor 40, i.e., where the final dehydrogenation reaction is carried out at a pressure at the end of the reactor, at or near atmospheric and at even less than atmospheric conditions if this is required to effect the desired degree of dehydrogenation, it is particularly important to maintain Taylor flow or pulsating flow as the case may be. Mass transfer of the hydrogen from the liquid phase to the gas phase at or near atmospheric pressure is quite limited. However, low hydrogen pressures favor completion of the dehydrogenation reaction.

The reaction product from third microchannel reactor 40 is passed to gas/liquid separator 46 via manifold 48 where hydrogen is recovered as an overhead via line 50. The dehydrogenated liquid fuel is recovered as a bottoms fraction from gas/liquid separator 46 via line 52 and ultimately is sent to a hydrogenation facility. Then the dehydrogenated liquid fuel is catalytically hydrogenated and returned for service as a liquid fuel source.

In the event that the hydrogenation product in line 50 contains traces of organic compounds, these may be removed if desired by passing the gas stream through an adsorbent bed (not shown) or an appropriate separator for the trace organic impurity.

Although, the dehydrogenation process has been described employing 3 microchannel reactors, other apparatus designs and operating conditions may be used and are within the context of the invention. The operation parameters are one of process design. The use of multiple reactors, as described, allows for better control of gas/liquid ratios as dehydrogenation of the liquid fuel occurs in the reaction chambers as well as providing for optimized pressures in dehydrogenation of the various organic fuel sources.

The invention claimed is:

1. A system for acquisition and delivery of hydrogen from an organic compound capable of reversible hydrogenation/dehydrogenation wherein the organic compound is initially in its hydrogenated form and subsequently catalytically dehydrogenated under dehydrogenation conditions forming hydrogen and byproduct dehydrogenated organic compound, the system comprising:
   a liquid fuel line;
   a heat exchange fluid line; and
   at least one microchannel reactor coupled to the liquid fuel line and the heat exchange fluid line, wherein the at least one microchannel reactor comprises a plurality of reaction channels and a plurality of heat exchange channels adjacent to the plurality of reaction channels, and wherein a reaction product exiting the at least one microchannel reactor comprises hydrogen and a dehydrogenated liquid fuel.

2. The system of claim 1, further comprising at least one phase separator coupled to the at least one microchannel reactor, wherein the at least one phase separator accepts the reaction product comprising hydrogen and the dehydrogenated liquid fuel from the at least one microchannel reactor for separation.

3. The system of claim 2, further comprising a first exit line coupled to the at least one phase separator for accepting the hydrogen.

4. The system of claim 2, further comprising a second exit line coupled to the at least one phase separator for accepting the dehydrogenated liquid fuel.

5. The system of claim 1, wherein the at least one microchannel reactor comprises three microchannel reactors in series.

6. The system of claim 2, wherein the pressure of each succeeding microchannel reactor in the series is less than the prior microchannel reactor.

7. The system of claim 2, wherein the temperature of each succeeding microchannel reactor in the series is higher than the prior microchannel reactor.

8. The system of claim 1, further comprising a supplemental heating device coupled to the heat exchange fluid line.

9. The system of claim 8, wherein the supplemental heating device is a thermoelectric unit.

10. The system of claim 1, further comprising an adsorbent bed coupled to the at least one phase separator for removal of trace organic compounds.

11. The system of claim 1, wherein the plurality of reaction channels are straight.

12. The system of claim 1, wherein the liquid fuel line comprises N-ethyl carbazole.

13. The system of claim 1, wherein the heat exchange fluid line comprises heat exchange fluid from a fuel cell.

14. The system of claim 1 wherein the volume of hydrogen produced in each microchannel reactor is essentially the same.

* * * * *